United States Patent
Trukhan et al.

(10) Patent No.: US 9,688,700 B2
(45) Date of Patent: Jun. 27, 2017

(54) METAL-ORGANIC FRAMEWORKS BASED ON ON 2,5-FURANDICARBOXYLIC ACID OR 2,5-THIOPHENEDICARBOXYLIC ACID

(75) Inventors: Natalia Trukhan, Ludwigshafen (DE); Ulrich Müller, Neustadt (DE); Jens Heimann, Worms (DE); Alois Kindler, Grünstadt (DE)

(73) Assignee: BASF SE, Ludwigshafen (DE)

( * ) Notice: Subject to any disclaimer, the term of this patent is extended or adjusted under 35 U.S.C. 154(b) by 809 days.

(21) Appl. No.: 13/512,637

(22) PCT Filed: Nov. 25, 2010

(86) PCT No.: PCT/EP2010/068234
§ 371 (c)(1),
(2), (4) Date: Jun. 12, 2012

(87) PCT Pub. No.: WO2011/064307
PCT Pub. Date: Jun. 3, 2011

(65) Prior Publication Data
US 2012/0251438 A1    Oct. 4, 2012

(30) Foreign Application Priority Data
Nov. 30, 2009  (EP) .................... 09177495

(51) Int. Cl.
C07F 1/00    (2006.01)
C07F 15/02   (2006.01)
C07F 5/06    (2006.01)
C07F 3/00    (2006.01)

(52) U.S. Cl.
CPC .............. C07F 1/005 (2013.01); C07F 3/003 (2013.01); C07F 5/069 (2013.01); C07F 15/025 (2013.01)

(58) Field of Classification Search
CPC ........ C07F 1/005; C07F 15/025; C07F 5/069; C07F 3/003
See application file for complete search history.

(56) References Cited

U.S. PATENT DOCUMENTS

| 5,648,508 | A * | 7/1997 | Yaghi ................................ 556/9 |
| 2010/0006454 | A1* | 1/2010 | Gruenwald et al. ............. 206/7 |
| 2011/0011805 | A1* | 1/2011 | Schubert .............. B01J 20/0233 210/689 |
| 2011/0112343 | A1 | 5/2011 | Leung et al. |
| 2011/0118526 | A1 | 5/2011 | Schubert et al. |
| 2011/0178335 | A1 | 7/2011 | Leung et al. |
| 2011/0265654 | A1 | 11/2011 | Eisenhardt et al. |
| 2012/0016066 | A1 | 1/2012 | Leung et al. |
| 2012/0016160 | A1 | 1/2012 | Leung et al. |
| 2012/0070353 | A1 | 3/2012 | Trukhan et al. |

FOREIGN PATENT DOCUMENTS

| WO | WO-03/035717 | 5/2003 |
| WO | WO 2007/044473 | 4/2007 |
| WO | WO 2007128617 A1 * | 11/2007 |
| WO | WO 2008/057140 | 5/2008 |
| WO | WO-2009/092777 A1 * | 7/2009 ............. B01D 53/28 |

OTHER PUBLICATIONS

"International Search Report in PCT/EP2010/068234", mailed on Jan. 27, 2011, 2 pages.
Jia, Hong-Peng et al., "Synthesis, Structure and Magnetism of Metal-Organic Franmework Materials with Doubly Pillared Layers", *Eur. J. Inorg. Chem.* 2006, pp. 4264-4270.
"Translated IPRP of PCT/EP2010/068234", mailed Feb. 5, 2013, 5 pages.
Wang, Dan, Research on the Synthesis and Structure of a Metal-organic Coordination Polymer of a Composite Ligand, *Dissertation of Master's Degree, Beijing University of Chemical Technology* Dec. 15, 2007, 19 pages.

* cited by examiner

*Primary Examiner* — Melvin C Mayes
*Assistant Examiner* — Michael Forrest
(74) *Attorney, Agent, or Firm* — Drinker Biddle & Reath LLP

(57) ABSTRACT

The present invention relates to porous metallic frameworks comprising at least one at least bidentate organic compound coordinated to at least one metal ion, wherein the at least one at least bidentate organic compound is derived from 2,5-furandicarboxylic acid or 2,5-thiophenedicarboxylic acid. The present invention further relates to shaped bodies comprising these frameworks, processes for producing them and their use, in particular for the storage and separation of gases.

12 Claims, 3 Drawing Sheets

Figure 1:
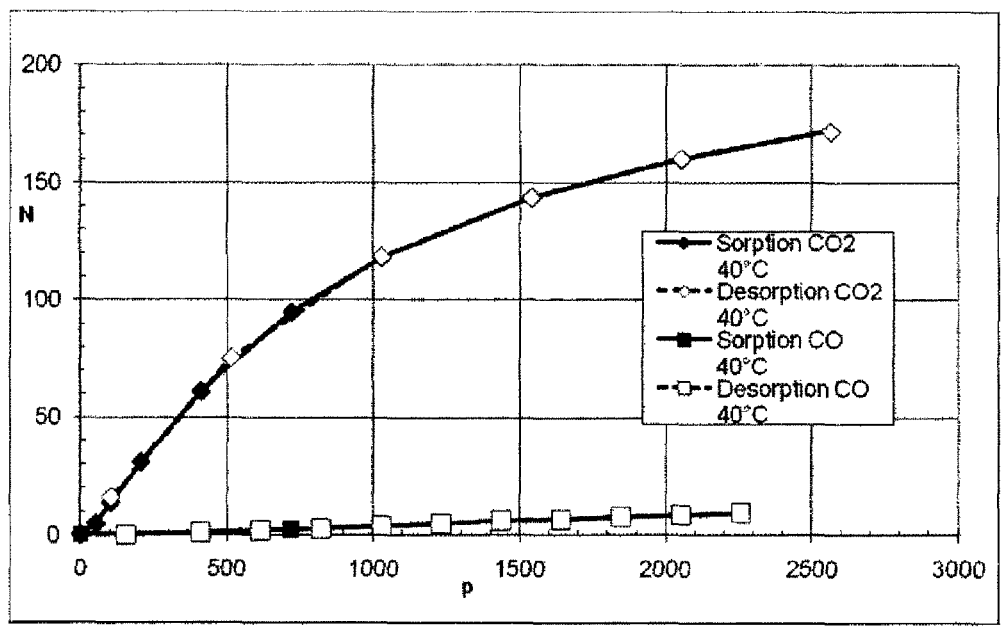

METAL-ORGANIC FRAMEWORKS BASED ON ON 2,5-FURANDICARBOXYLIC ACID OR 2,5-THIOPHENEDICARBOXYLIC ACID

CROSS-REFERENCE TO RELATED APPLICATIONS

This application is the national stage entry of PCT/EP2010/068234, filed on Nov. 25, 2010, which claims priority to European Patent Application No. 09177495.0, filed on Nov. 30, 2009, both of which are incorporated herein by reference in their entireties.

Field

The present invention relates to a porous metal-organic framework, shaped bodies comprising this, processes for producing it and its use.

Background

Porous metal-organic frameworks are known from the prior art. They are, in particular, distinguished by their porosity and can frequently be employed in applications comparable to those which are known for inorganic zeolites.

Metal-organic frameworks usually comprise an at least bidentate organic compound which is coordinated to a metal ion and joins at least two metal ions in a bridging fashion and thus together with the metal ions represents the skeleton of the metal-organic framework.

A suitable choice of metal and/or organic compound makes it possible to optimize the framework for the desired field of application. Here, for example, the choice of organic compound can have an influence on the pore distribution. Furthermore, the metal can make a contribution in adsorption processes.

There is thus a continuing need for specific metal-organic frameworks which, in particular, have extraordinary properties attributable to the choice of the metal and of the organic compound.

DETAILED DESCRIPTION

One or more aspects of the present invention provides such materials and processes for producing them and uses for them.

Accordingly, in one or more embodiments, provided is a porous metal-organic framework comprising at least one at least bidentate organic compound coordinated to at least one metal ion, wherein the at least one at least bidentate organic compound is derived from 2,5-furandicarboxylic 35 acid or 2,5-thiophenedicarboxylic acid.

It has been found that the metal-organic framework of the invention can be particularly suitable for use in the separation of $CO_2/CO$, $CH_4/H_2O$ and/or the storage of hydrogen.

The porous metal-organic frameworks of the invention have the above-described typical properties of metal-organic frameworks. Here, the porous metal-organic frameworks of the invention comprise 2,5-furandicarboxylic acid or 2,5-thiophenedicarboxylic acid as at least bidentate organic compound or are derived from these.

For the purposes of the present invention, the term "derive" means that 2,5-furandicarboxylic acid or 2,5-thiophenedicarboxylic acid can be present in partially deprotonated or completely deprotonated form in the framework. Furthermore, 2,5-furandicarboxylic acid or 2,5-thiophenedicarboxylic acid can comprise a substituent or a plurality of independent substituents. Examples of such substituents are $OH$, $NH_2$, $OCH_3$, $CH_3$, $NH(CH_3)$, $N(CH_3)_2$, $CN$ and halides. However, the at least bidentate organic compound is preferably derived from unsubstituted 2,5-furandicarboxylic acid or 2,5-thiophenedicarboxylic acid. Furthermore, the term "derive" means, for the purposes of the present invention, that one or more carboxyl functions can be present in the form of a corresponding sulfur analog. Sulfur analogs are the functional groups $C(=O)SH$ and its tautomer and $C(=S)SH$, which can be used in place of one or both carboxyl groups. However, preference is given to using no sulfur analogs.

The metal component in the framework according to the present invention is preferably selected from groups Ia, IIa, IIIa, IVa to VIIIa and Ib to VIb. Particular preference is given to Mg, Ca, Sr, Ba, Sc, Y, Ln, Ti, Zr, Hf, V, Nb, Ta, Cr, Mo, W, Mn, Re, Fe, Ro, Os, Co, Rh, Ir, Ni, Pd, Pt, Cu, Ag, Au, Zn, Cd, Hg, Al, Ga, In, Tl, Si, Ge, Sn, Pb, As, Sb and Bi, where Ln represents lanthanides.

Lanthanides are La, Ce, Pr, Nd, Pm, Sm, En, Gd, Tb, Dy, Ho, Er, Tm, Yb.

As regards the ions of these elements, particular mention may be made of $Mg^{2+}$, $Ca^{2+}$, $Sr^{2+}$, $Ba^{2+}$, $Sc^{3+}$, $Y^{3+}$, $Ln^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pr$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $Bi^{3+}$ and $Bi^{+}$.

Particular preference is also given to Mg, Al, Y, Sc, Zr, Ti, V, Cr, Mo, Fe, Co, Cu, Ni, Zn, Ln. Greater preference is given to Al, Mg, Fe, Cu and Zn. Al is very particularly preferred.

The process of the invention for preparing a framework according to the invention comprises, as step (a), reaction of a reaction solution comprising a metal salt corresponding to the at least one metal ion and 2,5-furandicarboxylic acid or 2,5-thiophenedicarboxylic acid and also a solvent at a temperature in the range from 100° C. to 150° C. for at least 3 hours and (b) isolation of the precipitated solid.

The reaction is preferably carried out with stirring for at least part of the time, in particular at the beginning of the reaction.

A metal salt is used as a starting compound. The initial concentration of this metal salt in the reaction mixture is preferably in the range from 0.05 mol/l to 0.8 mol/l. The initial concentration is more preferably in the range from 0.1 mol/l to 0.5 mol/l. In particular, the initial concentration is in the range from 0.15 mol/l to 0.3 mol/l.

The metal salt is introduced into the reaction solution in such an amount that the metal ion concentration in the reaction solution decreases in step (b) as a result of the precipitation of the solid.

Furthermore, it is preferred that the ratio of the initial molar amount of 2,5-furandicarboxylic acid or 2,5-thiophenedicarboxylic acid used to the initial molar amount of metal salt used, based on the metal, is in the range from 0.5:1 to 2:1. The ratio is more preferably in the range from 1:1 to 1.8:1, more preferably in the range from 1:1 to 1.7:1.

The reaction mixture for step (a) of the process of the invention for preparing the framework of the invention further comprises a solvent.

The solvent has to be suitable for at least partly dissolving the starting materials used. In addition, the solvent has to be selected in such a way that the required temperature range can be adhered to.

The reaction in the process of the invention for preparing the material according to the invention is thus carried out in the presence of a solvent. It is possible here to use solvothermal conditions. For the purposes of the present invention, the term "thermal" refers to a preparative process in which the reaction is carried out in a pressure vessel with the vessel closed during the reaction and elevated temperature being applied so that a pressure is built up within the reaction medium in the pressure vessel as a result of the vapor pressure of the solvent present. The desired reaction temperature can, if appropriate, be achieved in this way.

The reaction is preferably not carried out in a water-comprising medium and likewise not under solvothermal conditions.

The reaction in the process of the invention is accordingly preferably carried out in the presence of a nonaqueous solvent.

The reaction is preferably carried out at a pressure of not more than 2 bar (absolute). However, the pressure is preferably not more than 1230 mbar (absolute). The reaction particularly preferably takes place at atmospheric pressure. However, it is possible here for slightly superatmospheric or subatmospheric pressure to occur due to the apparatus. For the purposes of the present invention, the term "atmospheric pressure" therefore refers to a pressure range given by the actual prevailing atmospheric pressure ±150 mbar.

The reaction takes place in the temperature range from 100° C. to 150° C. The temperature is preferably in the range from 115° C. to 140° C. The temperature is more preferably in the range from 120° C. to 130° C.

The reaction solution can further comprise a base. This serves, in particular, for making the acid readily soluble when an acid is used. The use of an organic solvent frequently makes it unnecessary to use such a base. Nevertheless, the solvent for the process of the invention can be selected so that it has a basic reaction, but this is not absolutely necessary for carrying out the process of the invention.

It is likewise possible to use a base. However, preference is given to not adding any additional base.

Furthermore, it is advantageous for the reaction to take place with stirring, which is also advantageous in the case of a scale-up.

The (nonaqueous) organic solvent is preferably a $C_{1-6}$-alkanol, dimethyl sulfoxide (DMSO), N,N-dimethylformamide (DMF), N,N-diethylformamide (DEF), N,N-dimethylacetamide (DMAc), acetonitrile, toluene, dioxane, benzene, chlorobenzene, methyl ethyl ketone (MEK), pyridine, tetrahydrofuran (THF), ethyl acetate, halogenated or unhalogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones, such as cyclohexanone, sulfolene or mixtures thereof.

A $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

A halogenated or unhalogenated $C_{1-200}$-alkane is an alkane having from 1 to 200 carbon atoms in which one or more up to all hydrogen atoms can or may be replaced by halogen, preferably chlorine or fluorine, in particular chlorine. Examples of this are chloroform, dichloromethane, tetrachloromethane, dichloroethane, hexane, heptane, octane and mixtures thereof.

Preferred solvents are DMF, DEF, DMAc and NMP. Particular preference is given to DMF.

The term "nonaqueous" preferably refers to a solvent which does not exceed a maximum water content of 10% by weight, more preferably 5% by weight, even more preferably 1% by weight, even more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvent" refers to pure solvents and mixtures of different solvents.

Step (a) of this process of the invention for preparing the framework of the invention is carried out for at least 3 hours. The reaction is preferably carried out for at least 6 hours, more preferably at least 12 hours, more preferably at least 18 hours.

Furthermore, the process of the invention comprises the step (b), isolation of the precipitated solid.

As a result of step (a) of the preparative process of the invention, the framework precipitates from the reaction mixture as a solid. It can be isolated by methods known in the prior art, e.g. filtration or the like.

The metal-organic framework of the invention can be present in powder form or as agglomerate.

The porous metal-organic framework of the invention can be used as such in powder form or is converted into a shaped body.

Accordingly, it is a further aspect of the present invention that the porous metal-organic framework of the invention is present as powder.

A further aspect of the present invention is therefore a shaped body comprising the porous metal-organic framework of the invention.

The production of shaped bodies from metal-organic frameworks is described, for example, in WO-A 03/102000.

Preferred processes for producing shaped bodies are extrusion or tableting. In the production of shaped bodies, it is possible to add further materials such as binders, lubricants or other additives which are added during the production process. It is likewise conceivable for the framework to comprise further constituents, for example adsorbents such as activated carbon or the like.

The possible geometries of the shaped bodies are essentially not subject to any restrictions. For example, possible shapes are, inter alia, pellets such as disk-shaped pellets, pills, spheres, granules, extrudates such as rods, honeycombs, grids or hollow bodies.

To produce the shaped bodies, it is in principle possible to employ all suitable methods. In particular, the following processes are preferred:

kneading/pan milling of the framework either alone or together with at least one binder and/or at least one pasting agent and/or at least one template compound to give a mixture; shaping of the resulting mixture by means of at least one suitable method such as extrusion; optionally washing and/or drying and/or calcination of the extrudate; optionally finishing treatment.

tableting together with at least one binder and/or other auxiliaries.

application of the framework to at least one optionally porous support material. The material obtained can then be processed further by the above-described method to give a shaped body.

application of the framework to at least one optionally porous substrate.

Kneading/pan milling and shaping can be carried out by any suitable method, for example as described in Ullmanns Enzyklopädie der Technischen Chemie, 4$^{th}$ edition, Volume 2, p. 313 ff. (1972).

For example, the kneading/pan milling and/or shaping can be carried out by means of a piston press, roller press in the presence or absence of at least one binder, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or under superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder, with the binder used basically being able to be any chemical compound which ensures the desired viscosity for the kneading and/or shaping of the composition to be kneaded and/or shaped. Accordingly, binders can, for the purposes of the present invention, be either viscosity-increasing or viscosity-reducing compounds.

Preferred binders are, for example, inter alia aluminum oxide or binders comprising aluminum oxide, as are described, for example, in WO 94/29408, silicon dioxide as described, for example, in EP 0 592 050 A1, mixtures of silicon dioxide and aluminum oxide as are described, for example, in WO 94/13584, clay minerals as are described, for example, in JP 03-037156 A, for example montmorillonite, kaolin, bentonite, halloysite, dickite, nacrite and anauxite, alkoxysilanes as are described, for example, in EP 0 102 544 B1, for example tetraalkoxysilanes such as tetramethoxysilane, tetraethoxysilane, tetrapropoxysilane, tetrabutoxysilane, or for example trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, or for example trialkoxytitanates such as trimethoxytitanate, triethoxytitanate, tripropoxytitanate, tributoxytitanate, alkoxyzirconates, for example tetraalkoxyzirconates such as tetra methoxyzirconate, tetraethoxyzirconate, tetrapropoxyzirconate, tetrabutoxyzirconate, or for example trialkoxyzirconates such as trimethoxyzirconate, triethoxyzirconate, tripropoxyzirconate, tributoxyzirconate, silica soles, amphiphilic substances and/or graphites.

As viscosity-increasing compound, it is, for example, also possible to use, if appropriate, in addition to the abovementioned compounds, an organic compound and/or a hydrophilic polymer such as, for example, cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran and/or a polyethylene oxide.

As pasting agent, it is possible to use, inter alia, preferably water or at least one alcohol such as, for example: a monoalcohol having from 1 to 4 carbon atoms, for example methanol, ethanol, n-propanol, isopropanol, 1-butanol, 2-butanol, 2-methyl-1-propanol or 2-methyl-2-propanol, or a mixture of water and at least one of the alcohols mentioned or a polyhydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222. The order of the additives such as template compound, binder, pasting agent, viscosity-increasing substance during shaping and kneading is in principle not critical.

In a further, preferred embodiment, the shaped body obtained by kneading and/or shaping is subjected to at least one drying step which is generally carried out at a temperature in the range from 25 to 500° C, preferably in the range from 50 to 500° C. and particularly preferably in the range from 100 to 350° C. It is likewise possible to carry out drying under reduced pressure or under a protective gas atmosphere or by spray drying.

In a particularly preferred embodiment, at least one of the compounds added as additives is at least partly removed from the shaped body during this drying process.

The metal-organic framework of the invention and also the shaped bodies of the invention are suitable for storage of a gas.

A further aspect of the present invention is accordingly the use thereof for storage of a gas.

Likewise, a further aspect of the present invention is accordingly a method of storing a gas, which comprises the step of bringing the gas into contact with a framework according to the invention or a shaped body according to the invention.

Hydrogen is particularly suitable for this storage.

In addition, the framework of the invention or the shaped body of the invention is suitable for separating a gas from a gas mixture.

A further aspect of the present invention is accordingly the use of a framework according to the invention or a shaped body according to the invention for separating a gas from a gas mixture.

Likewise, a further aspect of the present invention is accordingly a method of separating a gas from a gas mixture, which comprises the step: bringing a framework according to the invention or a shaped body according to the invention into contact with the gas mixture.

The gas mixture is, in particular, a gas mixture comprising $CO_2$ and CO. Here, $CO_2$ is preferably removed from the gas mixture.

Furthermore, the gas mixture can be a mixture comprising methane and water. Preference is given to removing gaseous water from the gas mixture. The gas mixture can be, for example, water-comprising natural gas.

The present invention is illustrated with the aid of the figures and the examples below.

FIG. 1 shows the adsorption and desorption at 40° C. for a metal-organic framework according to the invention (Al-2,5-furandicarboxylic acid MOF). Here, the amount of adsorbed gas (N) in mg per gram of framework is shown as a function of the absolute pressure p in mbar.

As can be seen from FIG. 1, it is possible to separate off $CO_2$ due to the different adsorption isotherms.

Figure 2:
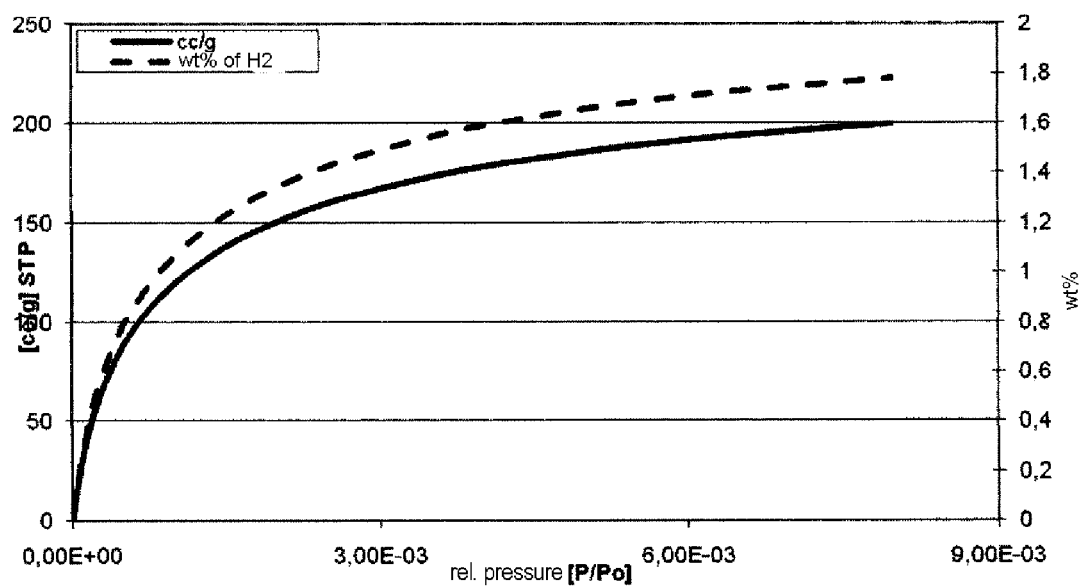

FIG. 2 shows the hydrogen adsorption at 77 K for the framework (Al-2,5-furandicarboxylic acid) as per Example 1, with preactivation being carried out at 130° C. for 4 hours ($P_0$ $H_2$ at 77 K =94 632.4 torr). FIG. 2 shows the amount of hydrogen absorbed (in $cm^3$/gSTP) (left-hand scale) and the proportion by weight of hydrogen (% by weight) (right-hand scale) as a function of the relative pressure p divided by p0.

Figure 3:
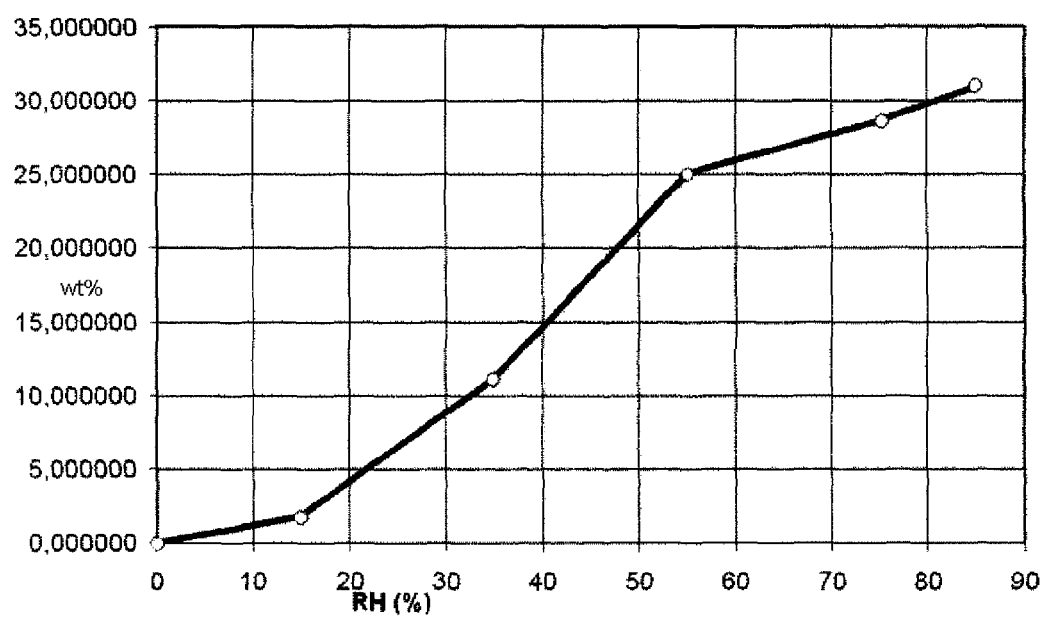

FIG. 3 shows the absorption of gaseous water by Al-2,5-thiophenedicarboxylic acid MOF at various relative humidities (RH). Here, the amount W in % by weight is shown as a function of RH in %.

EXAMPLES

Example 1

Al-2,5-Furandicarboxylic acid MOF

Experimental Method:

| Starting material | Molar | Calculated | Experimental |
|---|---|---|---|
| 1) Aluminum chloride * 6 water | 48.75 mmol | 11.8 g | 11.8 g |
| 2) 2,5-Furandicarboxylic acid | 82.87 mmol | 12.9 g | 12.9 g |
| 3) DMF | 6.8 mol | 500.0 g | 500.0 g |

In a 2 l four-neck flask, the furandicarboxylic acid and the aluminum chloride are suspended in the DMF. The solution with a proportion of solids is boiled at 130° C. for 24 hours, resulting in formation of a white suspension. After cooling, the white precipitate is filtered off and washed 1 ml with 200 ml of DMF and 4 times with 200 ml of methanol. The filter cake is dried at RT for 16 hours in a vacuum.

Weight obtained: 10.3 g
Color: white
Solids concentration: 2.0%
Space-time yield: 19.6 kg/m$^2$/d
Yield based on Al: 91%

Analyses:
Langmuir surface area (preactivation at 130° C.): 1153 m$^2$/g (BET: 850 m$^2$/g)

Chemical Analysis:

| Chloride ion | 0.47 g/100 g |
|---|---|
| Carbon | 34.7 g/100 g |
| Oxygen | 51 g/100 g |
| Nitrogen | 0.9 g/100 g |
| Hydrogen | 2.4 g/100 g |
| Al | 11.7 g/100 g |

H$_2$O adsorption, RT, 75% relative humidity: 35 wt %

Example 2

Mg-2,5-Furandicarboxylic acid MOF

Experimental Method:

| Starting material | Molar | Calculated | Experimental |
|---|---|---|---|
| 1) Magnesium nitrate * 6 water | 73.1 mmol | 18.7 g | 18.7 g |
| 2) 2,5-Furandicarboxylic acid | 82.87 mmol | 12.9 g | 12.9 g |
| 3) DMF | 6.8 mol | 500.0 g | 500.0 g |

In a 1 l four-neck flask, the furandicarboxylic acid and the magnesium nitrate are suspended in the DMF. The solution with a proportion of solids is boiled at 130° C. for 24 hours, resulting in formation of a white suspension. After cooling, the white precipitate is filtered off and washed once with 200 ml of DMF and four times with 200 ml of methanol. The filter cake is dried at RT for 16 hours in a high vacuum.

Weight obtained: 15.3 g
Color: white
Solids concentration: 2.9%
Space-time yield: 29.3 kg/m$^2$/d
Yield based on Mg: 79.5%

Analyses:
Langmuir surface area (preactivation at 130° C.): 10 m$^2$/g (BET: 7 m$^2$/g)

Chemical Analysis:

| Carbon | 43.2 g/100 g |
|---|---|
| Oxygen | 38.7 g/100 g |
| Nitrogen | 5.8 g/100 g |
| Hydrogen | 4.1 g/100 g |
| Mg | 8.1 g/100 g |

H$_2$O adsorption, RT, 75% relative humidity: 41 wt %

Example 3

Fe-2,5-Furandicarboxylic acid MOF

Experimental Method:

| Starting material | Molar | Calculated | Experimental |
|---|---|---|---|
| 1) Iron nitrate * 9 water | 48.7 mmol | 19.6 g | 19.6 g |
| 2) 2,5-Furandicarboxylic acid | 82.87 mmol | 12.9 g | 12.9 g |
| 3) DMF | 6.8 mol | 500.0 g | 500.0 g |

In a 1 l four-necked flask, the furandicarboxylic acid and the iron nitrate are suspended in the DMF. During heating to 130° C., the solution thickens to form a dark brown viscose gel. After the stirrer speed has been increased, the gel liquefies slightly. The gel is boiled at 130° C. for 24 hours. After cooling, the dark brown precipitate is filtered off and washed once with 200 ml of DMF and 4 times with 200 ml of methanol. The filter cake is dried at RT for 16 hours in a high vacuum.

Weight obtained: 17.5 g
Color: rust-brown
Solids concentration: 3.2%
Space-time yield: 32.3 kg/m$^2$/d
Yield based on Fe: 69.1%

Analyses:
Langmuir surface area (preactivation at 130° C.): 419 m$^2$/g (BET: 303 m$^2$/g)

Chemical Analysis:

| Carbon | 37.9 g/100 g |
|---|---|
| Oxygen | 33.9 g/100 g |
| Nitrogen | 7.1 g/100 g |
| Fe | 15.0 g/100 g |

Example 4

Zn-2,5-Furandicarboxylic acid MOF

Experimental Method:

| Starting material | Molar | Calculated | Experimental |
|---|---|---|---|
| 1) Zinc nitrate * 4 water | 73.1 mmol | 19.5 g | 19.5 g |
| 2) 2,5-Furandicarboxylic acid | 82.87 mmol | 12.9 g | 12.9 g |
| 3) DMF | 6.8 mol | 500.0 g | 500.0 g |

In a 1 l four-neck flask, the furandicarboxylic acid and the zinc nitrate are suspended in the DMF. The solution with a proportion of solids is boiled at 130° C. for 24 hours, resulting in formation of a white suspension. After cooling, the white precipitate is filtered off under a nitrogen atmosphere and washed once with 200 ml of DMF and 4 times with 200 ml of chloroform. The filter cake is dried at RT for 16 hours in a high vacuum.

Weight obtained: 15.6 g
Color: white
Solids concentration: 2.9%
Space-time yield: 29.3 kg/m$^2$/d
Yield based on Zn: 54.1%

Analyses:
Langmuir surface area (preactivation at 130° C.): 3 m$^2$/g (BET: 2 m$^2$/g)

Chemical Analysis:

| | |
|---|---|
| Carbon | 39.2 g/100 g |
| Oxygen | 33.9 g/100 g |
| Nitrogen | 5.7 g/100 g |
| Hydrogen | 3.9 g/100 g |
| Zn | 17.1 g/100 g |

Example 5

Cu-2,5-Furandicarboxylic acid MOF

Experimental Method:

| Starting material | Molar | Calculated | Experimental |
|---|---|---|---|
| 1) Copper chloride * 2 water | 73.1 mmol | 12.5 g | 12.5 g |
| 2) 2,5-Furandicarboxylic acid | 82.87 mmol | 12.9 g | 12.9 g |
| 3) DMF | 6.8 mol | 500.0 g | 500.0 g |

In a 1 l four-neck flask, the furandicarboxylic acid and the copper chloride are suspended in the DMF. The solution with a proportion of solids is boiled at 130° C. for 24 hours, resulting in formation of a blue suspension. After cooling, the blue precipitate is filtered off and washed once with 200 ml of DMF and 4 times with 200 ml of methanol. The filter cake is dried at RT for 16 hours in a high vacuum.

Weight obtained: 2.5 g
Color: blue
Solids concentration: 0.5%
Space-time yield: 7.6 kg/m$^2$/d
Yield based on Cu: 9.6%

Analyses:
Langmuir surface area (preactivation at 130° C.): 307 m$^2$/g (BET: 227 m2/g)

Chemical Analysis:

| | |
|---|---|
| Carbon | 36.2 g/100 g |
| Oxygen | 32.7 g/100 g |
| Nitrogen | 5.6 g/100 g |
| Cu | 17.9 g/100 g |

Example 6

Al-2,5-Thiophenedicarboxylic acid MOF

Apparatus:
500 ml four-neck flask
Low-temperature cooler
Oil bath
Stirrer, PTFE coated
Thermometer
Nitrogen blanketing Batch:

| | Molar Mass | Batch | | Comment |
|---|---|---|---|---|
| 2,5-Thiophene-dicarboxylic acid | 172.16 g/mol | 23.20 mmol | 3.99 g | |
| Aluminum chloride × 6 water | 241.43 g/mol | 13.65 mmol | 3.33 g | w = 99% |
| DMF | 73.0 | 1904 mmol | 138.99 g | 146 ml D = 0.95 g/cm$^3$ |
| Temperature: | 130° C./reflux | | | |
| Duration: | 24 hours | | | |

Procedure:
Place 146 ml of N,N-dimethylformamide in a four-neck flask and introduce 3.99 g of thiophenedicarboxylic acid (1) and 3.33 g of aluminum chloride×6 water (2) at room temperature while stirring. A colorless solution is formed. The reaction mixture is subsequently heated to 130° C. (reflux). The reaction mixture is maintained at 130° C. for 24 hours and then cooled to RT.

The white suspension/precipitate is separated off on a glass filter frit No. 3, and can be filtered readily.

DMF Washing:
The filter cake is slurried with 100 ml of N,N-DMF, left in contact for 15 minutes, subsequently filtered off with suction. The procedure is repeated twice using 100 ml of DMF each time.

Methanol Washing:
The filter cake is subsequently slurried with 100 ml of AR methanol, left in contact for 15 minutes, subsequently filtered off with suction. The procedure is repeated 4 times using 100 ml of AR methanol each time.

Drying:
The filter cake is dried at 130° C. for 24 hours in a vacuum drying oven at <20 mbar.

Color: colorless
Weight obtained: 3.1 g

Analysis:
BET/LM: 1021 /1375 m$^2$/g

General Data:
Yield (linker): 62.5%
Yield (metal salt): 105.8%
Solids content (product): 2.2% by weight
Space-time yield: 21.2 kg/m$^3$/d

The invention claimed is:

1. A method of separating gaseous water from a gas mixture, the method comprising exposing the gas mixture to a porous metal-organic framework comprising at least one at least bidentate organic compound coordinated to at least one metal ion that includes aluminum ion, wherein the at least one at least bidentate organic compound is derived from 2,5-furandicarboxylic acid or 2,5-thiophenedicarboxylic acid, wherein the porous metal-organic framework has a Langmuir surface area of from 1153 m$^2$/g to 1375 m$^2$/g, or a BET surface area of 850 m$^2$/g to 1021 m$^2$/g, follow preactivation at 130°C.

2. The method according to claim 1, wherein the porous metal-organic framework is comprised in a shaped body.

3. The method according to claim 1, wherein the porous metal-organic framework is prepared by a process, the process comprising:
(a) reaction of a reaction mixture comprising a metal salt corresponding to the at least one metal ion and 2,5- furandicarboxylic acid or 2,5- thiophenedicarboxylic acid and also a solvent at a temperature in the range from 100° C. to 150° C. for at least 3 hours and (b) isolation of the precipitated solid.

4. The method according to claim 3, wherein the initial concentration of the metal salt in the reaction mixture is in the range from 0.05 mol/L to 0.8 mol/L.

5. The method according to claim 3, wherein the ratio of the initial molar amount of 2,5-furandicarboxylic acid or 2,5-thiophenedicarboxylic acid used to the initial molar amount of metal salt used, based on the metal, is in the range from 0.5:1 to 2:1.

6. The method according to claim 5, wherein the gaseous mixture is natural gas that includes the gaseous water.

7. The method according to claim 3, wherein the solvent comprises N,N-dimethylformarmide.

8. The method according to claim 1, wherein the at least one at least bidentate organic compound is derived from unsubstituted 2,5-furandicarboxylic acid or unsubstituted 2,5- thiophenedicarboxylic acid.

9. The method according to claim 1, wherein the at least one at least bidentate organic compound is derived from 2,5-furandicarboxylic acid.

10. The method according to claim 1, wherein the at least one at least bidentate organic compound is derived from 2,5-thiophenedicarboxylic acid.

11. The method according to claim 1, wherein the gaseous mixture is natural gas that includes the gaseous water.

12. A method of separating gaseous water from a gas mixture, the method comprising exposing the gas mixture to a porous metal-organic framework comprising at least one at least bidentate organic compound coordinated to at least one metal ion that includes aluminum ion, wherein the at least one at least bidentate organic compound is derived from 2,5-thiophenedicarboxylic acid.

* * * * *